US010876174B2

(12) United States Patent
van den Bogaard et al.

(10) Patent No.: US 10,876,174 B2
(45) Date of Patent: Dec. 29, 2020

(54) **METHOD FOR THE DETECTION AND CHARACTERIZATION OF A TOXINOGENIC *CLOSTRIDIUM DIFFICILE* STRAIN**

(71) Applicant: KONINKLIJKE PHILIPS N.V., Eindhoven (NL)

(72) Inventors: Patrick Theodoor Christian van den Bogaard, Waalre (NL); Astrid Elisabeth Visser, Amsterdam (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/617,010

(22) Filed: Jun. 8, 2017

(65) Prior Publication Data

US 2018/0237827 A1  Aug. 23, 2018

Related U.S. Application Data

(62) Division of application No. 13/262,844, filed as application No. PCT/IB2010/051396 on Mar. 31, 2010, now abandoned.

(30) Foreign Application Priority Data

Apr. 7, 2009 (EP) .................................... 09157547

(51) Int. Cl.
*C12Q 1/689* (2018.01)
(52) U.S. Cl.
CPC ....... *C12Q 1/689* (2013.01); *C12Q 2600/156* (2013.01)
(58) Field of Classification Search
CPC .......................... C12Q 1/689; C12Q 2600/156
USPC ...................................................... 435/91.2
See application file for complete search history.

(56) References Cited

U.S. PATENT DOCUMENTS

| 5,210,015 | A | 5/1993 | Gelfand et al. |
| 5,304,481 | A | 4/1994 | Davies et al. |
| 5,925,517 | A | 7/1999 | Tyagi et al. |
| 6,174,670 | B1 | 1/2001 | Wittwer et al. |
| 8,101,362 | B2 | 1/2012 | Cockerill et al. |
| 8,133,703 | B2 | 3/2012 | Ching et al. |
| 8,211,647 | B2 | 7/2012 | Fukui et al. |
| 9,096,638 | B2 | 8/2015 | Paquette et al. |
| 2005/0026277 | A1 | 2/2005 | Festoc |
| 2006/0177844 | A1* | 8/2006 | Ching .................... B01L 3/502 435/6.12 |
| 2007/0026426 | A1 | 2/2007 | Fuernkranz et al. |
| 2009/0203021 | A1* | 8/2009 | Cockerill, III .......... C12Q 1/689 435/6.13 |
| 2010/0132628 | A1 | 6/2010 | Tien et al. |
| 2012/0028819 | A1 | 2/2012 | Van Den Bogaard et al. |

FOREIGN PATENT DOCUMENTS

WO  2007136303 A1  11/2007

OTHER PUBLICATIONS

Ahern, The Scientist, vol. 20, pp. 20 and 22, July (Year: 1995).*
Dial, S. et al, (2005), "Use of gastric acid suppressive agents and the risk of community acquired Colostridium difficile associated disease", JAMA Dec. 21, 2005, vol. 294 (23): 2989-95.
McPherson, M.J. et al, editors, PCR: A Practical Approach and PCR2: A Practical Approach (IRL Press, Oxford, 1991 and 1995).
Mackay, I.M. et al, "Survey and Summary Real-time PCR in Virology", Nucleic Acids Research, 30: 1292-1305 (2002).
Bernard, P.S. et al. "Color multiplexing hybridization probes using the aploprotein E locus as a model system for genotyping". Anal Biochem 1999; 273: 221-228.
Freeman, W.M., et al, "Quantitative RT-PCR: pitfalls and potential". Biotechniques; 26: 112-126 15 (1999).
Bouvet, P.J. et al., entitled as "Genetic relatedness of Clostridium difficile isolates from various origins determined by triple-locus sequences analysis based on toxin regulatory genes tcdC, tcdR and cdtR," J. Clin Microbiol., 2008, vol. 46, No. 11, pp. 3703-3713.
Curry, S.R., et al., entitled as "todC genotypes associated with severe TcdC truncation in an epidemic clone and other strains of Clostridium difficile," J. Clin. Microbiol., 2007, vol. 45, No. 1, pp. 215-221.
Maccannell, D.R., et al., entitled as "Molecular analysis of Clostridium difficile PCR ribotype 027 isolates from Eastern ane Western Canada," J. Clin. Microbiol., 2006, vol. 44, No. 6, pp. 2147-2152.
Van Den Berg, R.J. et al., "Characterization of toxin A-negative, toxin B-positive Clostridium difficile isolates from outbreaks in different countries by amplified fragment length polymorphism and PCR ribotyping," J. Clin. Microbiol., 2004, vol. 42, No. 3, pp. 1035-1041.
The Journal for Infection Control Team, Jan. 15, 2008, vol. 3, No. 1, p. 81-85. (Articles and explanation are attached.).
Antikainen, J. et al., "Detection of Virulence Genes of Clostridium Difficile by Multiplex PCR", APMIS: ACTA Pathologica, Microbiologica, et Immunologica Scandinavica Aug. 2009 LMD-PUBMD: 19664132, vol. 117, No. 8, Aug. 2009 (Aug. 2009) XP002585929, ISSN: 1600-0463, pp. 607-613.

(Continued)

*Primary Examiner* — Cynthia B Wilder

(57) ABSTRACT

The invention relates to a cartridge for the detection and characterization of a toxinogenic *Clostridium difficile* strain in a sample, wherein the following steps are performed, (i) a sample is provided for, (ii) in a multiplex PCR assay, (iii) the sample is analyzed with respect to the presence or absence of the cytotoxin tcdB gene, (iv) the sample is analyzed with respect to the presence or absence of one or more of the following deletions in the tcdC gene: (a) an 18 bp deletion in SEQ ID NO. 1 from nucleotide 330 to nucleotide 347, (b) a 36 bp deletion in SEQ ID NO. 1 from nucleotide 301 to nucleotide 336, (c) a 39 bp deletion in SEQ ID NO. 1 from nucleotide 341 to nucleotide 370, (d) a 54 bp deletion in SEQ ID NO. 1 from nucleotide 313 to nucleotide 366 and (e) a single nucleotide deletion at position 117 of SEQ ID NO. 1. The invention also relates to respective kits and primers and probes.

5 Claims, 2 Drawing Sheets

Specification includes a Sequence Listing.

(56) References Cited

OTHER PUBLICATIONS

Belanger, S.D. et al., "Rapid Detection of Clostridium difficile in Feces by Real-Time PCR", Journal of Clinical Microbiology, vol. 41, No. 2, pp. 730-734, Feb. 2003.

Spigaglia, P. et al., "Molecular Analysis of the Pathogenicity Locus and Polymorphism in the Putative Negative Regulator of Toxin Production (TcdC) Amoung Clostridium Difficile Clinical Isolates", Journal of Clinical Microbiology, Sep. 2002, pp. 3470-3475.

Wolff, D. et al., "Rapid Detection of the Clostridium Difficile Ribotype 027 tcdC Gene Frame Shift Mutation at Position 117 by Real-Time PCR and Melt Curve Analysis" European Journal of Clinical Microbiology & Infectious Diseases: Official Publication of the European Society fo Clinical Microbiology, Aug. 2009 LNKD PUBMED: 19333630, vol. 28, No. 8, Aug. 2009 (Aug. 2009), XP))2585936 ISSN: 1435-4373 abstract p. 960, col. 2, table 2, pp. 959-962.

Cohen, S.H. et al., "Analysis of the Pathogenicity Locus in Clostridium Difficile Strains", Journal of Infectious Diseases, vol. 181, No. 2, Feb. 2000 (Feb. 2000) XP002585934 ISSN: 0022-1899, pp. 659-663.

Fenner, L. et al., Epidemiology of Clostridium Difficile-Associated Disease at University Hospital Basel including Molecular Characterisation of teh Isolates 2006-200, European Journal of Clinical Microbiology & Infectious Diseases: Official Publication of the European Society of Clinical Microbiology Dec. 2008 LNKDPUBMED: 18560909, vol. 27, No. 12, Dec. 2008 (Dec. 2008), pp. 1201-1207.

Lemee, L. et al., "Multiplex PCR Targeting tpi (Triose Phosphate Isomerase) tcdA (Toxin A), and TcdB (Toxin B) Genes for Toxigenic Culture of Clostridium Difficile", Journal of Clinical Microbiology Dec. 2004—LNKP-PUBMED: 15583303, vol. 42, No. 12, Dec. 2004 (Dec. 2004, pp. 5710-5714.

Persson, S. et al., "New Multiplex PCR Method for the Detection of Clostridium Difficile Toxin A (tcdA) and Toxin B (tcdB) and the Binary Toxin (cctA/cdtB) Genes Applied to a Danish Strain Collection" Clinical Microbiology and Infection Official Publicaiton of the European Society of Clinical Microbiology and Infectious Diseases No. 2008 LNKDPUBMED: 19040478, vol. 14, No. 11 Nov. 2008 (Nov. 2008), XP00258885931 ISSN: 1469-0691, pp. 1057-1064.

Sloan, L.M. et al., "Comparison of real-time PCR for detection of the tcdC gene with four toxin immunoassays and culture in diagnosis of Clostridium difficile infection", Journal of Clinical Microbiologyk Jun. 1, 2008 American Society for Microbiology, US, vol. 46, Nr: 6, p. 1996-2001.

Sambol, S.P. et al., "Toxin Gene Analysis of a Variant Strain of Clostridium difficile That Causes Human Clinical Disease", Infection and Immunity vol. 68, No. 10, 2000, pp. 5480-5487.

Van Den Berg, R.J. et al., "Characterization of Toxin A-Negative, Toxin B-Positive Clostridium difficile Isolates from Outbreaks in Different Countries by Amplified Fragment Length Polymorphism and PCR Ribotyping", Journal of Clinical Microbiology vol. 42, No. 3, 2004, pp. 1035-1041. I.

Rupnik, M. et al., "Binary toxin producing Clostridium difficile strains", Anaerobe, vol. 9, Issue 6, Dec. 2003, pp. 289-294.

Antikainen, J. et al., "Detection of virulence genes of Clostridium difficile by Multiplex PCR" Clinical microbiology and Infection, vol. 117, Issue 8, Aug. 2009, pp. 607-613.

* cited by examiner

SEQUENCE LISTING

```
<160> NUMBER OF SEQ ID NOS: 15

<210> SEQ ID NO 1
<211> LENGTH: 699
<212> TYPE: DNA
<213> ORGANISM: Clostridium difficile

<400> SEQUENCE: 1
atgttttcta aaaaaatga tggtaacgaa tttagtaatg aaggaaaagg aagctctaag        60
aaaataatta aattctttaa gagcacaaag ggtattgctc tactggcatt tattttaggc       120
gtgttttttg gcaatatatc ctcaccagct tgttctgaag accatgagga ggtcatttct       180
aaccaaacat cagttataga ttctcaaaaa acagaaatag aaactttaaa tagcaaattg       240
tctgatgctg aaccatggtt caaaatgaaa gacgacgaaa agaaagctat tgaagctgaa       300
aatcaacgta aagctgaaga agctaaaaaa gctgaagaag ctaaaaaggc tgaagaacaa       360
cgcaaaaaag aagaagagga gaagaaagga tatgatactg gtattactta tgaccaatta       420
gctagaacac ctgatgatta taagtacaaa aaggtaaaat ttgaaggtaa ggttattcaa       480
gttattgaag atggtgatga ggtgcaaata agattagctg tgtctggaaa ttatgataag       540
gttgtactat gtagttataa aaaatcaata actccttcaa gagtattaga ggatgattac       600
ataactataa gaggtataag tgctggaact ataacttatg aatcaactat gggtggaaat       660
ataactatac cagggatagc tgtagagaaa attaattaa                             699

<210> SEQ ID NO 2
<211> LENGTH: 120
<212> TYPE: DNA
<213> ORGANISM: Clostridium difficile

<400> SEQUENCE: 2
cattagatga aactatagac ttacttccta cattatctga aggattacct ataattgcaa        60
ctattataga tggtgtaagt ttaggtgcag caatcaaaga gctaagtgaa acgagtgacc       120

<210> SEQ ID NO 3
<211> LENGTH: 140
<212> TYPE: DNA
<213> ORGANISM: Clostridium difficile

<400> SEQUENCE: 3
ttttgcccca gctaatacac ttgatgaaaa cctagaagga gaagcaattg attttactgg        60
```

```
aaaattaatt attgacgaaa atatttatta ttttgatgat aattatagag gagctgtaga      120
atggaaagaa ttagatggtg                                                  140

<210> SEQ ID NO 4
<211> LENGTH: 140
<212> TYPE: DNA
<213> ORGANISM: Clostridium difficile

<400> SEQUENCE: 4
tgaaagaaaa ggaagctcta agaaaataat taaattcttt aagagcacaa aggatattgc       60
tctactggca tttattttgg tgtgtttttt ggcaatatat cctcaccagc ttgttctgaa      120
gaccatgagg aggtcatttc                                                  140

<210> SEQ ID NO 5
<211> LENGTH: 200
<212> TYPE: DNA
<213> ORGANISM: Clostridium difficile

<400> SEQUENCE: 5
caaaatgaaa gacgacgaaa agaaagctat tgaagctgaa aatcaacgta aagctgaaga       60
agctaaaaaa gctgaagaag ctaaaaaggc tgaagaacaa cgcaaaaaag aagaagagga      120
gaagaaagga tatgatactg gtattactta tgaccaatta gctagaacac ctgatgatta      180
tagtacaaaa ggtaaatttg                                                  200

<210> SEQ ID NO 6
<211> LENGTH: 200
<212> TYPE: DNA
<213> ORGANISM: Clostridium difficile

<400> SEQUENCE: 6
gttgatgtct gattgggaag acgaagattt ggatacagat aatgataata taccagattc       60
atatgaacga aatggatata ctattaagga cttaattgca gttaagtggg aagatagttt      120
tgcagaacaa ggctataaga aatatgtatc aaattattta gagtcaaata ctgctggaga      180
tccatataca gattatgaaa                                                  200

<210> SEQ ID NO 7
<211> LENGTH: 540
<212> TYPE: DNA
<213> ORGANISM: Clostridium difficile

<400> SEQUENCE: 7
tttatcaaag taaattctta actttgaatg gcaaaaaata ttattttgat aatgactcaa       60
aagcagttac tggatggcaa accattgatg gtaaaaaata ttactttaat cttaacactg      120
ctgaagcagc tactggatgg caaactattg atggtaaaaa atattacttt aatactaaca      180
cttccatagc ttcaactggt tatacaatta ttaatggtaa acatttttat tttaatactg      240
atggtattat gcagatagga gtgtttaaag gacctaatgg atttgaatac tttgcacctg      300
ctaatacgga tgctaacaat atagaaggtc aagctatacg ttatcaaaat agattcctat      360
atttacatga caatatatat tactttggta ataattcaaa agcagttact ggatggcaaa      420
ctattaatgg taatgtatat tactttatgc ctgatactgc tatggctgca gctggtggac      480
ttttcgagat tgatggtgtt atatatttct ttggtgttga tggagtaaaa gcccctggga      540

<210> SEQ ID NO 8
```

```
<211> LENGTH: 145
<212> TYPE: DNA
<213> ORGANISM: Clostridium difficile

<400> SEQUENCE: 8
gaagctgaaa atcaacgtaa agctgaagaa gctaaaaagg ctgaagaaca acgtaaaaaa      60
gaagaagaag agaagaaagg atatgatact ggtattactt atgaccaatt agctagaaca     120
cctgatgatt ataagtacaa aaagg                                           145

<210> SEQ ID NO 9
<211> LENGTH: 138
<212> TYPE: DNA
<213> ORGANISM: Clostridium difficile

<400> SEQUENCE: 9
agaaagctat tgaagctgaa gaagctaaga aagctgaaga acaacgtaaa aagaagaag       60 aagagaagaa aggatatgat actggtatta cttatgacca attagctaga acatctgatg    120
attataagta caaaaagg                                                  138

<210> SEQ ID NO 10
<211> LENGTH: 95
<212> TYPE: DNA
<213> ORGANISM: Clostridium difficile

<400> SEQUENCE: 10
agctaaaaag gctgaagaag agaagaaagg atatgatact ggtattactt atgaccaatt      60
agctagaaca tctgatgatt ataagtacaa aaagg                                95

<210> SEQ ID NO 11
<211> LENGTH: 110
<212> TYPE: DNA
<213> ORGANISM: Clostridium difficile

<400> SEQUENCE: 11
tgaagctgaa aatcaacgta aaaagaagaa gagaggagaag aaaggatatg atactggtat     60
tacttatgac caattagcta gaacatctga tgattataag tacaaaaagg               110

<210> SEQ ID NO 12
<211> LENGTH: 680
<212> TYPE: DNA
<213> ORGANISM: Clostridium difficile

<400> SEQUENCE: 12 atgtttttcta aaaaaaatga gggtaacgaa tttagtaatg aaagaaaagg aagctctaag     60
aaaataatta aattctttaa gagcacaaag gatattgctc tactggcatt tattttggtg    120
tgttttttgg caatatatcc tcaccagctt gttctgaaga ccatgaggag gtcattttcta   180 atcaaacatc agttatagat tctcaaaaaa cagaaataga aactttaaat agcaaattgt    240
ctgatgctga accatggttc aaaatgaaag acgacgaaaa gaaagctatt gaagctgaaa    300
atcaacgtaa agctgaagaa gctaaaaagg ctgaagaaca acgtaaaaaa gaagaagaag    360
agaagaaagg atatgatact ggtattactt atgaccaatt agctagaaca cctgatgatt    420
ataagtacaa aaaggtaaaa tttgaaggta aggttattca agttattgaa gatggtgatg    480
aggtgcaaat aagattagct gtgtctggaa attatgataa ggtcgtacta tgtagttata    540
aaaaatcaat aactccttca agagtgttag aggatgatta cataactata agaggtataa    600
gtgctggaac tataacttat gaatcaacta tgggtggaaa aataaccata ccagggatag    660
```

```
ctgtagagaa aattaattaa                                               680

<210> SEQ ID NO 13
<211> LENGTH: 663
<212> TYPE: DNA
<213> ORGANISM: Clostridium difficile

<400> SEQUENCE: 13
atgttttcta aaaaaaatga gggtaacgaa tttagtaatg aaggaaaagg aagctctaag      60
aaaataatta aattctttaa gagcacaaag gatattgctc tactggcatt tattttggt     120 gtgtttttg gcaatatatc ctcaccagct tgttctgaag accatgagga ggtcatttct     180
aatcaaacat aagttataga ttctcaaaaa acagaaatag aaactttaaa tagcaaattg     240
tctgatgctg aaccatggtt caaaatgaaa gatgacgaaa agaaagctat tgaagctgaa     300
gaagctaaga agctgaaga caacgtaaa aaagaagaag aagagaagaa aggatatgat      360
actggtatta cttatgacca attagctaga acatctgatg attataagta caaaaaggta    420
aaatttgaag gtaaggttat tcaagttatt gaagatggtg atgaggtgca aataagatta    480
gctgtgtctg gaaattatga tgaggtcgta ctatgtagtt ataaaaaatc aataactcct    540
tcaagagtgt tagaggatga ttacataact ataagaggta taagtgctgg aactataact    600
tatgaatcaa ctatgggtgg aaaaataact ataccaggaa tagctgtaga gaaaataaat    660
taa                                                                  663

<210> SEQ ID NO 14
<211> LENGTH: 660
<212> TYPE: DNA
<213> ORGANISM: Clostridium difficile

<400> SEQUENCE: 14
atgttttcta aaaaaaatga gggtaacgaa tttagtaatg aaggaaaagg aatctctaag     60
aaaataatta aattctttaa gagcacaaag ggtattgctc tactggcatt tattttggt    120 gtgtttttg gcaatatatc ctcaccagct tgttctgaag accatgagga ggtcatttct     180
aattaaacat cagttataga ttctcaaaaa acagaaatag aaactttaaa tagcaaattg    240
tctgatgctg aaccatggtt caaaatgaaa gacgacgaaa agaaagctat tgaagctgaa    300
aatcaacgta aagctgaaga agctaaaaag gctgaagaag aagaaaagg atatgatact    360 ggtattactt atgaccaatt agctagaaca tctgatgatt ataagtacaa aaaggtaaaa    420
tttgaaggta aggttattca agttattgaa gatggtgatg aggtgcaaat aagattcgct    480
gtgtctggaa attatgataa ggttgtacta tgtagttaaa aaaatcaat aactccttca    540 agagtgttag aggatgatta cataactata gaggtataa gtgctggaac tataacttat    600
gaatcaacta tgggtggaaa cataactata ccaggaatag ctgtagagaa aattaattaa    660

<210> SEQ ID NO 15
<211> LENGTH: 645
<212> TYPE: DNA
<213> ORGANISM: Clostridium difficile

<400> SEQUENCE: 15
atgttttcta aaaaaaatga tggtaacgaa tttagtaatg aaggaaaagg aagctctaag     60
aaaataatta aattctttaa gagcacaaag ggtattgctc tactggcatt tattttaggc    120 gtgtttttg gcaatatatc ctcaccagct tgttctgaag accatgagga ggtcatttct     180
```

-continued

```
aaccaaacat cagttataga ttctcaaaaa acagaaatag aaactttaaa tagcaaattg    240
tctgatgctg aaccatggtt caaaatgaaa gacgacgaaa agaaagctat tgaagctgaa    300
aatcaacgta aaaaagaaga agaggagaag aaaggatatg atactggtat tacttatgac    360
caattagcta gaacatctga tgattataag tacaaaaagg taaaatttga aggtaaggtt    420
attcaagtta ttgaagatgg tgatgaggtg caaataagat tagctgtgtc tggaaattat    480
gataaggttg tactatgtag ttataaaaaa tcaataactc cttcaagagt attagaggat    540
gattacataa ctataagagg tataagtgct ggaactataa cttatgaatc aactatgggt    600
ggaaatataa ctataccagg gatagctgta gagaaaatta attaa                   645
```

METHOD FOR THE DETECTION AND CHARACTERIZATION OF A TOXINOGENIC *CLOSTRIDIUM DIFFICILE* STRAIN

CROSS REFERENCE TO RELATED APPLICATION

This is a divisional of prior application Ser. No. 13/262,844 filed Oct. 4, 2011.

FIELD OF THE INVENTION

The present invention is in the field of biology and chemistry. In particular, the invention is in the field of molecular biology. More particular, the invention is in the field of detection of nucleic acids and real-time PCR. Most particularly the invention relates to the detection and characterization of a toxinogenic *Clostridium diffcile* strain.

BACKGROUND OF THE INVENTION

*Clostridium diffcile* is a species of Gram-positive bacteria of the genus *Clostridium*. Clostridia are anaerobic, spore-forming rods (*bacillus*). *C. diffcile* is the most serious cause of antibiotic-associated diarrhea (AAD) and can lead to pseudomembranous colitis, a severe infection of the colon, often resulting from eradication of the normal gut flora by antibiotics. The *C. diffcile* bacteria, which naturally reside in the body, become overgrown: The overgrowth is harmful because the bacterium releases toxins that can cause bloating, constipation, and diarrhea with abdominal pain, which may become severe. Latent symptoms often mimic some flu-like symptoms. Discontinuation of causative antibiotic treatment is often curative.

*C. diffcile* infections can range in severity from asymptomatic to severe and life-threatening, especially among the elderly. People most often get infected in hospitals, nursing homes, or institutions, although *C. diffcile* infection in the community, outpatient setting is increasing. The rate of *C. diffcile* acquisition is estimated to be 13% in patients with hospital stays of up to 2 weeks, and 50% in those with hospital stays longer than 4 weeks. Frequency and severity of *C. difficile* colitis remains high and seems to be associated with increased death rates. Early intervention and aggressive management are key factors to recovery.

The emergence of a new, highly toxic strain of *C. diffcile*, resistant to fluoroquinolone antibiotics, such as Cipro (ciprofloxacin) and Levaquin (levofloxacin), said to be causing geographically dispersed outbreaks in North America was reported in 2005 (Dial S, Delaney J, Barkun A, Suissa S (2005). "Use of gastric acid-suppressive agents and the risk of community-acquired *Clostridium difficile*-associated disease". JAMA 294 (23): 2989-95. doi:10.1001/jama.294.23.2989).

On Jun. 4, 2003, two outbreaks of a highly virulent strain of this bacterium were reported in Montreal, Quebec and Calgary, Alberta, in Canada. Sources put the death count as low as 36 and as high as 89, with approximately 1,400 cases in 2003 and within the first few months of 2004. *C. difficile* infections continued to be a problem in the Quebec health care system in late 2004. As of March 2005, it had spread into the Toronto, Ontario area, hospitalizing 10 people.

A similar outbreak took place at Stoke Mandeville Hospital in the United Kingdom between 2003 and 2005.

It has been suggested that both the Canadian and English outbreaks were related to the seemingly more virulent Strain NAP1/BI/027 of the bacterium. This strain, also known as Quebec strain, has also been implicated in an epidemic at two Dutch hospitals (Harderwijk and Amersfoort, both 2005). A theory for explaining the increased virulence of 027 is that it is a hyperproducer of both toxins A and B, and that certain antibiotics may actually stimulate the bacteria to hyperproduce.

As one analyzes the pool of patients with the spores, many that are asymptomatic will pass the organism to individuals that are immunocompromised and, hence, susceptible to increasing rates of diarrhea and poor outcome. It seems notable that the clusters described above represent a challenge to epidemiologists trying to understand how the illness spreads via the convergence of information technology with clinical surveillance.

On Oct. 1, 2006, *C. difficile* was said to have killed at least 49 people at hospitals in Leicester, England over eight months, according to a National Health Service investigation.

On Oct. 27, 2006, 9 deaths were attributed to the bacterium in Quebec, Canada.

On Feb. 27, 2007, a new outbreak was identified at *Trillium* Health Centre in Mississauga, Ontario, where 14 people were diagnosed with the bacteria. The bacteria were of the same strain as the one in Quebec. Officials have not been able to determine whether *C. difficile* was responsible for deaths of four patients over the prior two months.

In October 2007, Maidstone and Tunbridge Wells NHS Trust was heavily criticized by the Healthcare Commission regarding its handling of a major outbreak of *C. difficile* in its hospitals in Kent from April 2004 to September 2006. In its report, the Commission estimated that about 90 patients "definitely or probably" died as a result of the infection (Healthcare Commission press release: Healthcare watchdog finds significant failings in infection control at Maidstone and Tunbridge Wells NHS Trust, 11 Oct. 2007 and Daily Telegraph, Health Secretary intervenes in superbug row, 11 Oct. 2007).

Thus, there is a need for a method for the detection and characterization of a toxinogenic *Clostridium difficile* strain in a sample.

SUMMARY OF THE INVENTION

The inventors have found a pioneering method for the detection and characterization of a toxinogenic *Clostridium difficile* strain in a sample. The advantage is that multiple diagnostic questions may be addressed in one single method. This method now allows designation of a sample as comprising a hypervirulant *Clostridium difficile* strain. Further, it allows scoring of a sample as a non NAP/BI/027 strain. Also the sample may be scored as NAP1/BI/027 strain. It may be also scored as ribotype 078 strain, or scored as 017 strain. Hence, in a single assay all of the above designations may be done.

The invention relates to a method for the detection and characterization of a toxinogenic *Clostridium difficile* strain in a sample, wherein the following steps are performed, (a) a sample is provided for, (b) in a multiplex PCR assay, (c) the sample is analyzed with respect to the presence or absence of the cytotoxin tcdB gene, (d) the sample is analyzed with respect to the presence or absence of one or more of the following deletions in the tcdC gene: (a) an 18 bp deletion in SEQ ID NO: 1 from nucleotide 330 to nucleotide 347, (b) a 36 bp deletion in SEQ ID NO: 1 from nucleotide 301 to nucleotide 336, (c) 39 bp deletion in SEQ ID NO: 1 from nucleotide 341 to nucleotide 370, (d) 54 bp deletion in SEQ ID NO: 1 from nucleotide 313 to nucleotide 366 and (e) a single nucleotide deletion at position 117 of SEQ ID NO: 1.

The invention also relates to a kit for performing the methods of the invention, comprising primers and or probes for amplifying and/or detecting (i) the cytotoxin tcdB gene, (ii) the 1.8 kb deletion in the tcdA gene, (iii) an 18 bp deletion in SEQ ID NO: 1 from nucleotide 330 to nucleotide 347 of the tcdC gene, (iv) a 39 bp deletion in SEQ ID NO: 1 from nucleotide 341 to nucleotide 370 of the tcdC gene, (v) a single nucleotide deletion at position 117 of SEQ ID NO: 1 and primers and/or probes for (vi) the detection of the binary toxin cdtA/B gene.

"Polymerase chain reaction" or "PCR" means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C.

The term "PCR" encompasses derivative forms of the reaction, including but not limited to, real-time PCR, nested PCR, quantitative PCR, multiplexed PCR, and the like. Reaction volumes range from a few hundred nanoliters, e.g. 200 nl, to a few hundred microlitres. Herein, preferred volumes are 10-50 microliter more preferably about 25 microliters per reaction chamber.

"Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons). Detection chemistries for real-time PCR are reviewed in Mackay et al, Nucleic Acids Research, 30: 1292-1305 (2002). In real time PCR a two temperature stage reaction may also be used in which the polymerisation temperature equals the annealing temperature, even for typical hybridization probes like Scorpion primers or Pleiades probes.

"Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) (two-color real-time PCR). Usually, distinct sets of primers are employed for each sequence being amplified. Typically, the number of target sequences in a multiplex PCR is in the range of from 2 to 10, or from 2 to 8, or more typically, from 3 to 6. The preferred number is 2-6 for the present invention.

"Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: pactin, GAPDH, microglobulin, ribosomal RNA, and the like. Techniques for quantitative PCR are well-known to those of ordinary skill in the art, as exemplified in the following references: 'Freeman et al, Biotechniques, 26: 112-126 15 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); BeckerAndre et al, Nucleic Acids Research, 17: 9437-9446 (1989); and the like.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references: Dieffenbach, editor, PCR Primer: A Laboratory Manual, $2^{nd}$ Edition (Cold Spring Harbor Press, New York, 2003).

"Sample" means a quantity of material from a biological, environmental, medical, or patient source in which detection or measurement of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention. The terms "sample" and "specimen" are used interchangeably.

Preferred amplification products are depicted in the following table:

TABLE 1

| SEQ ID NO | C. difficile target name | target length (bp) | target sequence |
|---|---|---|---|
| 2 | tcdB (amplicon 1) | 120 | CATTAGATGAAACTATAGACTTCCTTCCTACATTATCTGAAGGATTACCTATAATTGCAACTATTATAGATGGTGTAAGTTTAGGTGCAGCAATCAAAGAGCTAAGTGAAACGAGTGACC |
| 3 | tcdB (amplicon 2) | 140 | TTTTGCCCCAGCTAATACACTTGATGAAAACCTAGAAGGAGAAGCAATTGATTTTACTGGAAAATTAATTATTGACGAAATATTTATTATTTTGATGATAATTATAGAGGAGCTGTAGAATGGAAAGAATTAGATGGTG |
| 4 | tcdC_nt117 | 140 | TGAAAGAAAGGAAGCTCTAAGAAAATAATTAAATTCTTTAAGAGCACAAAGGATATTGCTCTACTGGCATTTATTTTGGTGTGTTTTTTGGCAATATATCCTCACCAGCTTGTTCTGAAGACCATGAGGAGGTCATTTC |
| 5 | tcdC deletions 18 bp, 36 bp, 39 bp and 54 bp | 200; same target region for all | CAAAATGAAAGACGACGAAAAGAAAGCTATTGAAGCTGAAAATCAACGTAAAGCTGAAGAAGCTAAAAAAGCTGAAGAAGCTAAAAAGGCTGAAGAACAACGCAAAAAAGAAGAAGAGGAGAAGAAAGGATATGATACTGGTATTACTTATGACCAATTAGCTAGAACACCTGATGATTATAGTACAAAAGGTAAATTTG |
| 6 | binary toxin | 200 | GTTGATGTCTGATTGGGAAGACGAAGATTTGGATACAGATAATGATAATATACCAGATTCATATGAACGAAATGGATATACTATTAAGGACTTAATTGCAGTTAAGTGGGAAGATAGTTTTGCAGAACAAGGCTATAAGAAATATGTATCAAATTATTTAGAGTCAAAATACTGCTGGAGATCCATATACAGATTATGAAA |
| 7 | tcdA deletion(s) | 540 | TTTATCAAAGTAAATTCTTAACTTTGAATGGCAAAAAATATTATTTTGATAATGACTCAAAAGCAGTTACTGGATGGCAAACCATTGATGGTAAAAAATATTACTTTAATCTTAACACTGCTGAAGCAGCTACTGGATGGCAAACTATTGATGGTAAAAAATATTACTTTAATACTAACACTTCCATAGCTTCAACTGGTTATACAATTATTAATGGTAAACATTTTTATTTTAATACTGATGGTATTATGCAGATAGGAGTGTTTAAAGGACCTAATGGATTTGAATACTTTGCACCTGCTAATACGGATGCTAACAATATAGAAGGTCAAGCTATACGTTATCAAAATAGATTCCTATATTTACATGACAATATATATTACTTTGGTAATAATTCAAAAGCAGTTACTGGATGGCAAACTATT |

TABLE 1-continued

| SEQ ID NO | C. difficile target name | target length (bp) | target sequence |
|---|---|---|---|
| | | | AATGGTAATGTATATTACT TTATGCCTGATACTGCTAT GGCTGCAGCTGGTGGACT TTTCGAGATTGATGGTGTT ATATATTTCTTTGGTGTTG ATGGAGTAAAAGCCCCTG GGA |
| 8 | tcdC 18-bp amplicon | 145 | GAAGCTGAAAATCAACGT AAAGCTGAAGAAGCTAAA AAGGCTGAAGAACAACGT AAAAAAGAAGAAGAAGA GAAGAAAGGATATGATAC TGGTATTACTTATGACCAA TTAGCTAGAACACCTGAT GATTATAAGTACAAAAAG G |
| 9 | tcdC 36-bp amplicon | 138 | AGAAAGCTATTGAAGCTG AAGAAGCTAAGAAAGCTG AAGAACAACGTAAAAAAG AAGAAGAAGAAGAAA GGATATGATACTGGTATTA CTTATGACCAATTAGCTAG AACATCTGATGATTATAA GTACAAAAAGG |
| 10 | tcdC 39-bp amplicon | 95 | AGCTAAAAAGGCTGAAGA AGAGAAGAAAGGATATGA TACTGGTATTACTTATGAC CAATTAGCTAGAACATCT GATGATTATAAGTACAAA AAGG |
| 11 | tcdC 54-bp amplicon | 110 | TGAAGCTGAAAATCAACG TAAAAAAGAAGAAGAGGA GAAGAAAGGATATGATAC TGGTATTACTTATGACCAA TTAGCTAGAACATCTGATG ATTATAAGTACAAAAAGG |
| 1 | full wt tcdC sequence (strain 630 ACCESSION AM180355 REGION: 804310..805008) | 699 | ATGTTTTCTAAAAAAAATG ATGGTAACGAATTTAGTA ATGAAGGAAAAGGAAGCT CTAAGAAAATAATTAAAT TCTTTAAGAGCACAAAGG GTATTGCTCTACTGGCATT TATTTTAGGCGTGTTTTTT GGCAATATATCCTCACCA GCTTGTTCTGAAGACCATG AGGAGGTCATTTCTAACC AAACATCAGTTATAGATTC TCAAAAAACAGAAATAGA AACTTTAAATAGCAAATT GTCTGATGCTGAACCATG GTTCAAAATGAAAGACGA CGAAAAGAAAGCTATTGA AGCTGAAAATCAACGTAA AGCTGAAGAAGCTAAAAA AGCTGAAGAAGCTAAAAA GGCTGAAGAACAACGCAA AAAAGAAGAAGAGGAGA AGAAAGGATATGATACTG GTATTACTTATGACCAATT AGCTAGAACACCTGATGA TTATAAGTACAAAAAGGT AAAATTTGAAGGTAAGGT TATTCAAGTTATTGAAGAT GGTGATGAGGTGCAAATA AGATTAGCTGTGTCTGGA AATTATGATAAGGTTGTAC TATGTAGTTATAAAAAATC AATAACTCCTTCAAGAGT ATTAGAGGATGATTACAT AACTATAAGAGGTATAAG TGCTGGAACTATAACITAT GAATCAACTATGGGTGGA |

TABLE 1-continued

| SEQ ID NO | C. difficile target name | target length (bp) | target sequence |
|---|---|---|---|
| | | | AATATAACTATACCAGGG ATAGCTGTAGAGAAAATT AATTAA |
| 12 | full ribotype 027 tcdC sequence (incl nt1 17 and 18-bp deletion) ACCESSION DQ861412 | 680 | ATGTTTTCTAAAAAAATG AGGGTAACGAATTTAGTA ATGAAAGAAAAGGAAGCT CTAAGAAAATAATTAAAT TCTTTAAGAGCACAAAGG ATATTGCTCTACTGGCATT TATTTTGGTGTGTTTTTTG GCAATATATCCTCACCAGC TTGTTCTGAAGACCATGAG GAGGTCATTTCTAATCAAA CATCAGTTATAGATTCTCA AAAAACAGAAATAGAAAC TTTAAATAGCAAATTGTCT GATGCTGAACCATGGTTC AAAATGAAAGACGACGAA AAGAAAGCTATTGAAGCT GAAAATCAACGTAAAGCT GAAGAAGCTAAAAAGGCT GAAGAACAACGTAAAAAA GAAGAAGAAGAGAAGAA AGGATATGATACTGGTATT ACTTATGACCAATTAGCTA GAACACCTGATGATTATA AGTACAAAAAGGTAAAAT TTGAAGGTAAGGTTATTCA AGTTATTGAAGATGGTGA TGAGGTGCAAATAAGATT AGCTGTGTCTGGAAATTAT GATAAGGTCGTACTATGT AGTTATAAAAAATCAATA ACTCCTTCAAGAGTGTTAG AGGATGATTACATAACTA TAAGAGGTATAAGTGCTG GAACTATAACTTATGAATC AACTATGGGTGGAAAAAT AACCATACCAGGGATAGC TGTAGAGAAAATTAATTA A |
| 13 | full tcdC sequence of 36-bp deletion variant (ACCESSION DQ861424) | 663 | ATGTTTTCTAAAAAAATG AGGGTAACGAATTTAGTA ATGAAGGAAAAGGAAGCT CTAAGAAAATAATTAAAT TCTTTAAGAGCACAAAGG ATATTGCTCTACTGGCATT TATTTTGGTGTGTTTTTTG GCAATATATCCTCACCAGC TTGTTCTGAAGACCATGAG GAGGTCATTTCTAATCAAA CATAAGTTATAGATTCTCA AAAAACAGAAATAGAAAC TTTAAATAGCAAATTGTCT GATGCTGAACCATGGTTC AAAATGAAAGATGACGAA AAGAAAGCTATTGAAGCT GAAGAAGCTAAGAAAGCT GAAGAACAACGTAAAAAA GAAGAAGAAGAGAAGAA AGGATATGATACTGGTATT ACTTATGACCAATTAGCTA GAACATCTGATGATTATA AGTACAAAAAGGTAAAAT TTGAAGGTAAGGTTATTCA AGTTATTGAAGATGGTGA TGAGGTGCAAATAAGATT AGCTGTGTCTGGAAATTAT GATGAGGTCGTACTATGT AGTTATAAAAAATCAATA ACTCCTTCAAGAGTGTTAG AGGATGATTACATAACTA TAAGAGGTATAAGTGCTG GAACTATAACTTATGAATC AACTATGGGTGGAAAAAT |

TABLE 1-continued

| SEQ ID NO | C. difficile target name | target length (bp) | target sequence |
|---|---|---|---|
| | | | AACTATACCAGGAATAGC TGTAGAGAAAATAAATTA A |
| 14 | full tcdC sequence of 39-bp deletion variant (ACCESSION EF470292) | 660 | ATGTTTTCTAAAAAAATG AGGGTAACGAATTTAGTA ATGAAGGAAAAGGAATCT CTAAGAAAATAATTAAAT TCTTTAAGAGCACAAAGG GTATTGCTCTACTGGCATT TATTTTTGGTGTGTTTTTG GCAATATATCCTCACCAGC TTGTTCTGAAGACCATGAG GAGGTCATTTCTAATTAAA CATCAGTTATAGATTCTCA AAAAACAGAAATAGAAAC TTTAAATAGCAAATTGTCT GATGCTGAACCATGGTTC AAAATGAAAGACGACGAA AAGAAAGCTATTGAAGCT GAAAATCAACGTAAAGCT GAAGAAGCTAAAAAGGCT GAAGAAGAGAAGAAAGG ATATGATACTGGTATTACT TATGACCAATTAGCTAGA ACATCTGATGATTATAAGT ACAAAAAGGTAAAATTTG AAGGTAAGGTTATTCAAG TTATTGAAGATGGTGATG AGGTGCAAATAAGATTCG CTGTGTCTGGAAATTATGA TAAGGTTGTACTATGTAGT TAAAAAAAATCAATAACT CCTTCAAGAGTGTTAGAG GATGATTACATAACTATA AGAGGTATAAGTGCTGGA ACTATAACTTATGAATCAA CTATGGGTGGAAACATAA CTATACCAGGAATAGCTG TAGAGAAAATTAATTAA |
| 15 | full tcdC sequence of 54-bp deletion variant (not in public database) | 645 | ATGTTTTCTAAAAAAATG ATGGTAACGAATTTAGTA ATGAAGGAAAAGGAAGCT CTAAGAAAATAATTAAAT TCTTTAAGAGCACAAAGG GTATTGCTCTACTGGCATT TATTTTTAGGCGTGTTTTT GGCAATATATCCTCACCA GCTTGTTCTGAAGACCATG AGGAGGTCATTTCTAACC AAACATCAGTTATAGATTC TCAAAAAACAGAAATAGA AACTTTAAATAGCAAATT GTCTGATGCTGAACCATG GTTCAAAATGAAAGACGA CGAAAAGAAAGCTATTGA AGCTGAAAATCAACGTAA AAAAGAAGAAGAGGAGA AGAAAGGATATGATACTG GTATTACTTATGACCAATT AGCTAGAACATCTGATGA TTATAAGTACAAAAAGGT AAAATTTGAAGGTAAGGT TATTCAAGTTATTGAAGAT GGTGATGAGGTGCAAATA AGATTAGCTGTGTCTGGA AATTATGATAAGGTTGTAC TATGTAGTTATAAAAAATC AATAACTCCTTCAAGAGT ATTAGAGGATGATTACAT AACTATAAGAGGTATAAG TGCTGGAACTATAACTTAT GAATCAACTATGGGTGGA AATATAACTATACCAGGG ATAGCTGTAGAGAAAATT AATTAA |

TABLE 1-continued

| SEQ ID NO | C. difficile target name | target length (bp) | target sequence |
|---|---|---|---|
| 2 | SEQ ID NO: 2 is the preferred tcdB amplicon. | | |
| 3 | SEQ ID NO: 3 is a further preferred tcdB annplicon. | | |
| 4 | SEQ ID NO: 4 dislcoses the tcdC nt117 deletion. | | |
| 5 | SEQ ID NO: 5 discloses the tcdC deletions 18 bp, 36 bp, 39 bp and 54 bp. | | |
| 6 | SEQ ID NO: 6 discloses the binary toxin. | | |
| 7 | SEQ ID NO: 6 discloses the tcdA deletion(s). | | |
| 8 | SEQ ID NO: 8 is the preferred tcdC 18-bp amplicon. | | |
| 9 | SEQ ID NO: 9 is the preferred tcdC 36-bp. | | |
| 10 | SEQ ID NO: 10 is the preferred tcdC 39-bp amplicon | | |
| 11 | SEQ ID NO: 11 is the preferred tcdC 54-bp amplicon | | |
| 1 | SEQ ID NO: 1 is the full length wt tcdC sequence (strain 630 ACCESSION AM180355 REGION: 804310..805008) | | |
| 12 | SEQ ID NO: 12 is full length ribotype 027 tcdC sequence (incl nt1 17 and 18-bp deletion) ACCESSION DQ861412 | | |
| 13 | SEQ ID NO: 13 is the full lebth tcdC sequence of 36-hp deletion variant (ACCESSION DQ861424) | | |
| 14 | SEQ ID NO: 14 is the full length tcdC sequence of 39-bp deletion variant (ACCESSION EF470292) | | |
| 15 | SEQ ID NO: 15 is the full length tcdC sequence of 54-bp deletion variant. | | |

DETAILED DESCRIPTION OF EMBODIMENTS

Figure 1:
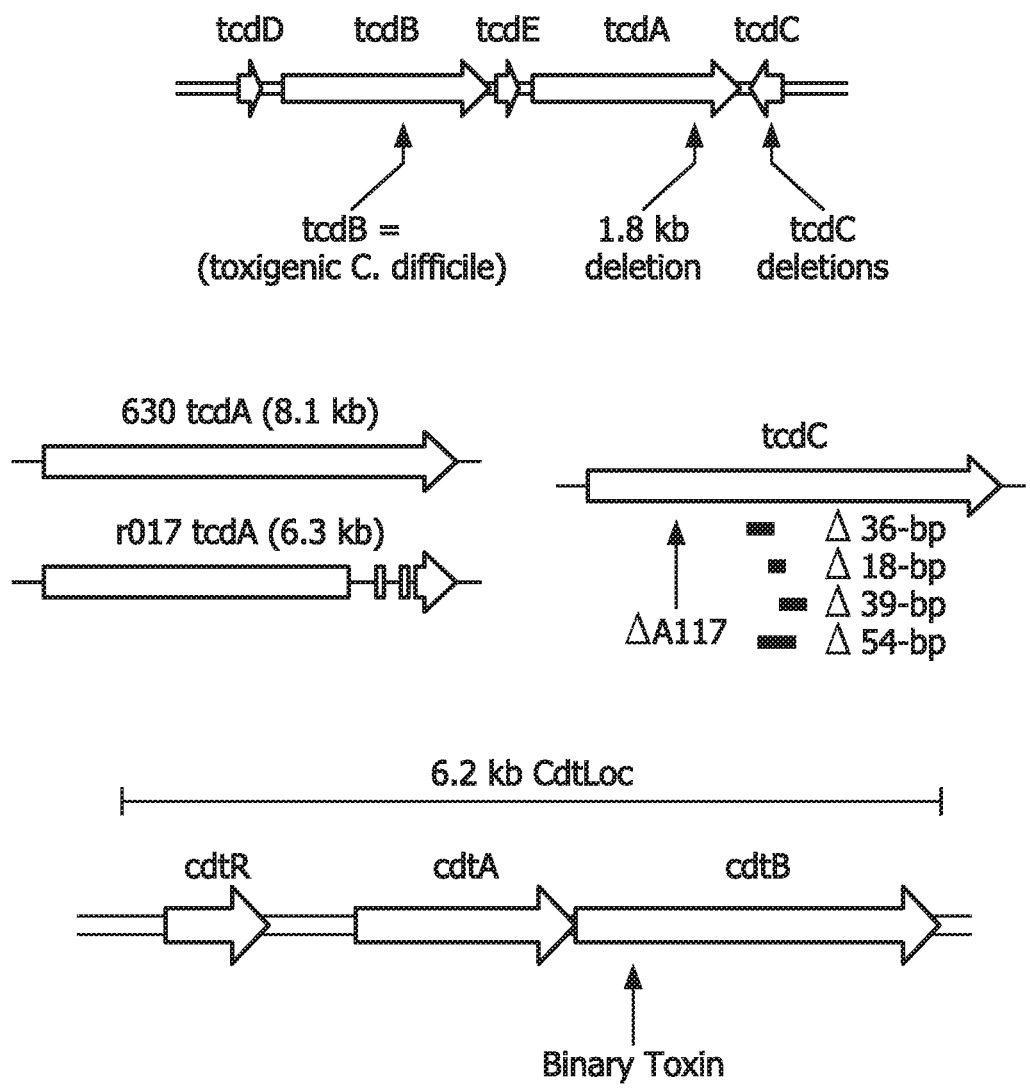
FIG. 1 shows the preferred targets according to the present invention.

The invention relates to a method for the detection and characterization of a toxinogenic *Clostridium difficile* strain in a sample, wherein the following steps are performed, (a) a sample is provided for, (b) in a multiplex PCR assay, (c) the sample is analyzed with respect to the presence or absence of the cytotoxin tcdB gene, (d) the sample is analyzed with respect to the presence or absence of one or more of the following deletions in the tcdC gene: (a) an 18 bp deletion in SEQ ID NO: 1 from nucleotide 330 to nucleotide 347, (b) a 36 bp deletion in SEQ ID NO: 1 from nucleotide 301 to nucleotide 336, (c) 39 bp deletion in SEQ ID NO: 1 from nucleotide 341 to nucleotide 370, (d) 54 bp deletion in SEQ ID NO: 1 from nucleotide 313 to nucleotide 366 and (e) a single nucleotide deletion at position 117 of SEQ ID NO: 1.

Optionally, the sample is additionally analyzed with respect to the presence or absence of the enterotoxin tcdA gene 1.8 kb deletion.

Preferably, the sample is additionally analyzed with respect to the presence or absence of the binary toxin cdtA and/or cdtB.

In one embodiment of the method according to the invention the sample is analyzed with respect to, (i) the presence or absence of all of following the deletions, (a) a 18 bp deletion in SEQ ID NO: 1 from nucleotide 330 to nucleotide 347, (b) a 39 bp deletion in SEQ ID NO: 1 from nucleotide 341 to nucleotide 370 and (c) a single nucleotide deletion at position 117 of SEQ ID NO: 1, (ii) the sample is analyzed with respect to the presence or absence of the cytotoxin tcdB gene, (iii) the sample is analyzed with respect to the presence or absence of the 1.8 kb tcdA deletion and (iv) the sample is analyzed with respect to the presence or absence of the cdtA/B binary toxin gene.

Preferably in the method according to the invention (a) if the tcdB gene sequence is present, the tcdA deletion is absent, neither the single nucleotide deletion at position 117 of SEQ ID NO: 1 is present, nor the 18 bp deletion is present, nor the 39 bp deletion is present, then the sample is scored as toxinogenic *Clostridium difficile*, (b) if the tcdB gene sequence is present, the tcdA deletion is absent, the single nucleotide deletion at position 117 of SEQ ID NO: 1 is present, the 18 bp deletion is present, the cdtA/B binary toxin gene is present, then the sample is scored as a ribotype 027 *Clostridium difficile* strain, (c) if the tcdB gene sequence is present, the tcdA deletion is present, neither the single nucleotide deletion at position 117 of SEQ ID NO: 1 is present, nor the 18 bp deletion is present, nor the 39 bp deletion in SEQ ID NO: 1 from nucleotide 341 to nucleotide 370 is present, the cdtA/B binary toxin gene is absent, then the sample is scored as a ribotype 017 *Clostridium diffcile* strain and (d) if the tcdB gene sequence is present, the tcdA deletion is absent, the 39 bp deletion in SEQ ID NO: 1 from nucleotide 341 to nucleotide 370 is present, the cdtA/B binary toxin gene is present, then the sample is scored as a ribotype 078 *Clostridium difficile* strain.

Optionally and additionally the following further targets may be analyzed. These are targets associated with hypervirulence, such as but not limited to tcdCA36 bp, tcdCA54 bp. The strains carrying the 36-bp, 39-bp or 54-bp deletions all have additional specific mutations upstream in the tcdC gene that result in a truncated and non-functional TcdC protein which is preferably part of the assay.

Specific variations in the 3' part of the tcdB gene have been reported relative to non-NAP1/BI/027 strains which are preferably in the assay.

Preferably the amplification products in the multiplex PCR assay are between 60 and 200 bp in size.

In one embodiment, the multiplex amplification reaction is done in a closed system in the presence of fluorescent indicators in the reaction mixture(s), the fluorescent indicators being capable of generating an optical signal related to a presence and/or quantity of each amplicon in the amplification reaction and monitoring the optical signal of the fluorescent indicators in the amplification reaction In the method according to the invention the closed system gives an optical output for the user, indicating the scoring assignment outlined above.

Preferably, the multiplex PCR amplification is quantitative real-time PCR. The real-time PCR (also designated herein as quantitative PCR or quantitative real-time PCR (qPCR)) is a method to simultaneously amplify and quantify nucleic acids using a polymerase chain reaction (PCR). Quantitative real-time reverse transcription PCR (RT-qPCR) is a quantitative real-time PCR method further comprising a reverse transcription of RNA into DNA, e.g. mRNA into cDNA. In qPCR methods, the amplified nucleic acid is quantified as it accumulates. Typically, fluorescent dyes that intercalate with double-stranded DNA (e.g. ethidiumbromide or SYBR® Green I) or modified nucleic acid probes ("reporter probes") that fluoresce when hybridized with a complementary nucleic acid (e.g. the accumulating DNA) are used for quantification in qPCR based methods. Particularly, fluorogenic primers, hybridization probes (e.g. LightCycler probes (Roche)), hydrolysis probes (e.g. TaqMan probes (Roche)), or hairpin probes, such as molecular beacons, Scorpion primers (DxS), Sunrise primers (Oncor), LUX primers (Invitrogen), Amplifluor primers (Intergen) or the like can be used as reporter probes. In accordance with the present invention, fluorogenic primers or probes may for example be primers or probes to which fluorescence dyes have been attached, e.g. covalently attached. Such fluorescence dyes may for example be FAM (5- or 6-carboxyfluorescein), VIC, NED, Fluorescein, FITC, IRD-700/800, CY3, CY5, CY3.5, CY5.5, HEX, TET, TAMRA, JOE, ROX, BODIPY TMR, Oregon Green, Rhodamine Green, Rhodamine Red, Texas Red, Yakima Yellow, Alexa Fluor, PET BIOSEARCH BLUE™, Marina Blue®, BOTHELL BLUE®, CAL Fluor® Gold, CAL Fluor® Red 610, QUASAR™ 670, LightCycler Red640®, QUASAR™ 705, LightCycler Red705® and the like. Particular reporter probes may additionally comprise fluorescence quenchers.

For the embodiments of the present invention selective primers can be used in quantitative real-time multiplex PCR.

A "primer" herein refers to an oligonucleotide comprising a sequence that is complementary to a nucleic acid to be transcribed ("template"). During replication polymerases attach nucleotides to the 3' end of the primer complementary to the respective nucleotides of the template.

In particular embodiments of the invention the polymerase used for quantitative real-time PCR is a polymerase from a thermophile organism or a thermostable polymerase or is selected from the group consisting of *Thermus thermophilus* (Tth) DNA polymerase, *Thermus acquaticus* (Taq) DNA polymerase, *Thermotoga maritima* (Tma) DNA polymerase, *Thermococcus litoralis* (Tli) DNA polymerase, *Pyrococcus furiosus* (Pfu) DNA polymerase, *Pyrococcus woesei* (Pwo) DNA polymerase, *Pyrococcus kodakaraensis* KOD DNA polymerase, *Thermus filiformis* (Tfi) DNA polymerase, *Sulfolobus solfataricus* Dpo4 DNA polymerase, *Thermus pacificus* (Tpac) DNA polymerase, *Thermus eggertssonii* (Teg) DNA polymerase, *Thermus brockianus* (Tbr) and *Thermus flavus* (Tfl) DNA polymerase.

Particularly, the fluorescently labelled probes are labelled with a dye selected from the group consisting of FAM, VIC, NED, Fluorescein, FITC, IRD-700/800, CY3, CY5, CY3.5, CY5.5, HEX, TET, TAMRA, JOE, ROX, BODIPY TMR, Oregon Green, Rhodamine Green, Rhodamine Red, Texas Red, Yakima Yellow, Alexa Fluor and PET.

In particular, the hybridization probe is a LightCycler probe (Roche) or the hydrolysis probe is a TaqMan probe (Roche). In other embodiments the hairpin probe is selected from the group consisting of molecular beacon, Scorpion primer, Sunrise primer, LUX primer and Amplifluor primer. The TaqMan probes are preferred.

The invention relates to a closed system amplification cartridge comprising one or more channels or chambers comprising primers and/or probes for amplifying and/or detecting (i) the cytotoxin tcdB gene, (ii) the 1.8 kb deletion in the tcdA gene, (iii) an 18 bp deletion in SEQ ID NO: 1 from nucleotide 330 to nucleotide 347 of the tcdC gene, (iv) a 39 bp deletion in SEQ ID NO: 1 from nucleotide 341 to nucleotide 370 of the tcdC gene, (v) a single nucleotide deletion at position 117 of SEQ ID NO: 1 and primers and/or probes for the detection of the binary toxin cdtA/B gene.

The invention also relates to a kit for performing the methods of the invention, comprising primers and or probes for amplifying and/or detecting (i) the cytotoxin tcdB gene, (ii) the 1.8 kb deletion in the tcdA gene, (iii) an 18 bp deletion in SEQ ID NO: 1 from nucleotide 330 to nucleotide 347 of the tcdC gene, (iv) a 39 bp deletion in SEQ ID NO: 1 from nucleotide 341 to nucleotide 370 of the tcdC gene, (v) a single nucleotide deletion at position 117 of SEQ ID NO: 1 and primers and/or probes for (vi) the detection of the binary toxin cdtA/B gene.

In preferred embodiments of the invention, the kit additionally comprises enzymes such as a polymerase a buffer and other ingredients.

In one embodiment the method may take place in a cartridge which is designed for performing sample preparation and real-time multiplex PCR. These are systems, methods, and apparatus for closed multi-stage nucleic acid amplification reactions wherein a portion of a prior-stage reaction mixture serves as the sample for the next stage reaction. The invention provides a method as outlined above for controlling the amplification comprising the step of (i) amplifying said multiplex reaction in the presence of a fluorescent indicator in a reaction mixture, the fluorescent indicator being capable of generating an optical signal related to a quantity of an amplicon in the amplification reaction; (ii) monitoring the optical signal of the fluorescent indicator in the amplification reaction.

The invention also relates to a closed system amplification cartridge comprising one or more channels or chambers comprising primers and or probes for amplifying and/or detecting (i) the cytotoxin tcdB gene, (ii) the tcdC gene, (iii) an 18 b deletion in SEQ ID NO: 1 from nucleotide 330 to nucleotide 347, (iv) a 36 bp deletion in SEQ ID NO: 1 from nucleotide 301 to nucleotide 336, (v) a 39 bp deletion in SEQ ID NO: 1 from nucleotide 341 to nucleotide 370, (vi)

a 54 bp deletion in SEQ ID NO: 1 from nucleotide 313 to nucleotide 366, (vii) a single nucleotide deletion at position 117 of SEQ ID NO: 1. Such a closed system is disclosed for example in WO 2006/047777. The cartridge may additionally comprise one or more chambers for sample preparation, e.g. cell lysis and/or nucleic acid extraction. Preferably the PCR chambers comprise a optically transparent surface, such as glass, crystal or plastic that allows for online detection of the amplification product.

Once the DNA has been isolated in the cartridge it is resolubilized in the mastermix, which is stored in lyophilized form inside the cartridge. Homogenizing the eluate in the mastermix solution then takes place. Filling the at least 3 to 5 PCR chambers (or a subset if the application so requires), such that no air is entrapped in the chambers is performed in the cartridge. Less than 5 chambers may be required by the amplification, here a cartridge variant may be used. The required elution volume can be adapted via the assay protocol. Closing the chambers during amplification, so that no amplicons may escape into the environment, and no air is allowed into the chambers is performed. Temperature-cycling the chambers is done. The cycling is synchronized between all chambers, with individual temperature set points. Fluorescence detection in up to 6 wavelengths is then done. Detection may be triggered at any moment in the cycle. Calculation of Ct values, initial concentrations and final test results, from the measurement data and, possibly, additional calibration data is performed. A test result is generated based on the Ct values for the targets of the invention.

The cartridge performs the PCR in a device. A specimen container or also cartridge herein arrives at the console, and the user enters the identifier (e.g. barcode, identifier on a paper order form, etc.) associated to the order. The console retrieves the associated order from the local console database. Next the user scans the RFID tag of the cartridge. The cartridge is checked on its validity (e.g. cartridge type corresponds with test type, expiration date, etc.). In case the cartridge is valid it is associated with the order in the console database. The console main service requests an available slot of an instrument. The instrument control subsystem returns an available slot after applying load-balancing. After notifying the user to insert the cartridge, the user inserts the cartridge in the suggested slot. The instrument control subsystem is notified that a cartridge was inserted and the console main service checks whether the cartridge is associated with the order. In case the cartridge is associated with the order, the recipe database is accessed to retrieve the recipe matching the test type in the order. After retrieving the recipe, the instrument control subsystem is ordered to upload the recipe and start the test for the slot where the cartridge was inserted. After completion of the test, the test result is received by the instrument control subsystem and the following steps will be performed:

The test result will be passed to the test result engine. The test result engine will store the result in the console database. Next the result will be send to the external IS via the external IS data exchange subsystem. And the user gets informed that the test is completed. The user gets an optical and/or acoustical output concerning the score.

Figure 2:
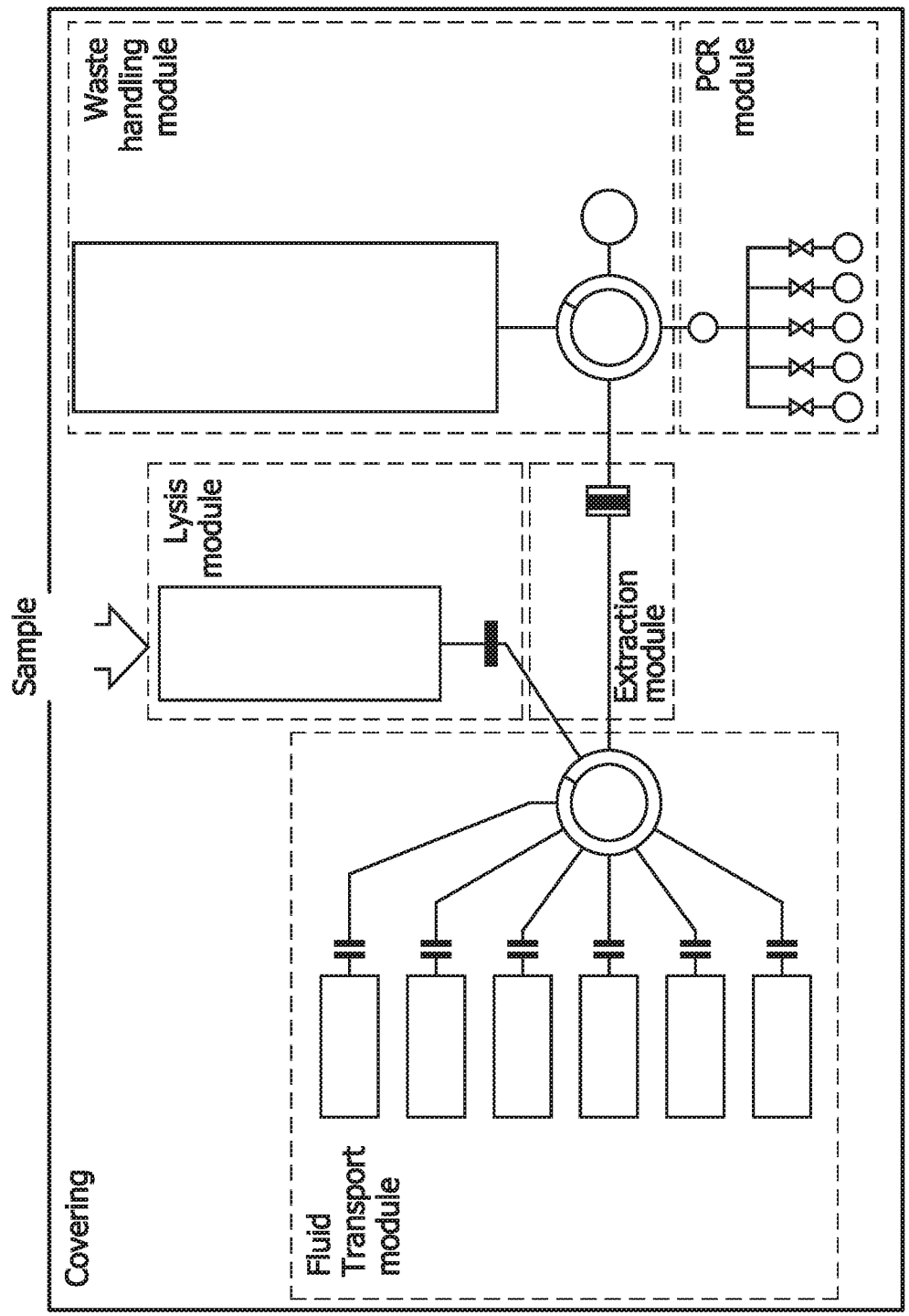
FIG. 2 shows a possible cartridge set-up according to the invention.

As drawn in FIG. 2, the cartridge is divided into 6 modules. The modules are explained in detail in the following paragraphs. A module within the cartridge is defined for its functionality. All functionality of the cartridge is integrated as much as possible and realized with a minimal number of parts. The total process flow is as follows: The operator fills the lysis chamber manually with the sample and closes the input lid. The cartridge is placed on the tray of the slot and with the tray loaded into the slot. When loaded into the slot, the process starts with liquefying and lysing the sample. This is all done with the help of, e.g. HiFU energy in the lysis chamber. Different reagents are added after each other to the sample so that the final result can be flushed through the extraction membrane. All this steps are done in one chamber to be able to handle also high viscose samples like stool (feces). Also only one interface and HiFU source is needed for all the processes. The transport of reagents to the chamber is done by the fluid transport module. Within this module the reagents are stored for the shelf life, are taken out of the reservoirs and transported to the lysis chamber. The module also transports the treated sample from the lysis chamber through the extraction membrane to the waste. In the same way the washing lysis module, fluid transport module, extraction module, waste handling module, PCR module, manual sample input, covering reagents are handled, taken from the reservoir and transported through the membrane to the waste. By centralizing the fluid actuation and handling, the number of interfaces and the number of components within the cartridge for this support function are minimized. The previous mentioned extraction membrane is embodied within the extraction module. This module ensures a good flow through the membrane and a good heat transfer to the membrane. This heat is needed for the ethanol removal and elution of the DNA. The waste handling module is used to direct all fluids, except the eluate, to the waste this is done by the same type of valve as used in the fluid handling module. This is done to minimize the different techniques used within the cartridge for the same functionality. The second function of this module is to suck the elute buffer through the extraction membrane. The actuation is done by this module to minimize the risk of contamination of the eluate. This risk would be higher when the fluid transport module also was used for this function. Before the eluate is transported to the PCR chamber, first the mastermix must be added and the DNA content must be homogenized over the total volume. This is also done within this module. Finally the fluid is transported to the PCR chamber. The actuation is done with the same actuator as used earlier for the elute transport through the extraction membrane. Pressure driven fluid transport is chosen also for this transport function. Next to that the functionality for pressure driven fluid transport is already within the cartridge. The PCR chambers, placed within the PCR module, must be filled without air. To ensure this a de-aeration membrane is placed within the supply channel to remove mixing-bubbles going to the PCR chamber. The PCR chambers are made so that the geometry of the chamber limits the volume. This makes sure that the chambers are filled with the same volume even when the chambers are filled from one supply channel. The chambers are placed parallel within the fluidic structure to prevent any cross talk of primers and/or probes that are specific per chamber. There is also a post-filling de-aeration filter.

The primers and/or probes here may include primers and/or probes for amplifying and/or detecting (i) the cytotoxin tcdB gene, (ii) the 1.8 kb deletion in the tcdA gene, (iii) an 18 bp deletion in SEQ ID NO: 1 from nucleotide 330 to nucleotide 347 of the tcdC gene, (iv) a 39 bp deletion in SEQ ID NO: 1 from nucleotide 341 to nucleotide 370 of the tcdC gene, (v) a single nucleotide deletion at position 117 of SEQ ID NO: 1 and primers and/or probes for the detection of the binary toxin cdtA/B gene. Further, the primers and/or probes here may include primers and/or probes for amplifying and/or detecting (i) the cytotoxin tcdB gene, (ii) the tcdC gene, (iii) an 18 bp deletion in SEQ ID NO: 1 from nucleotide 330 to nucleotide 347, (iv) a 36 bp deletion in SEQ ID NO: 1 from nucleotide 301 to nucleotide 336, (v) a 39 bp deletion in SEQ ID NO: 1 from nucleotide 341 to nucleotide 370, (vi) a 54 bp deletion in SEQ ID NO: 1 from nucleotide 313 to nucleotide 366, (vii) a single nucleotide deletion at position 117 of SEQ ID NO: 1.

Samples or specimens containing target polynucleotides (*Clostridum difficile*) may come from a wide variety of sources for use with the present invention, including cell cultures, animal or human tissues, patient biopsies, environmental samples, or the like. Samples are prepared for assays of the invention using conventional techniques, which typically depend on the source from which a sample or specimen is taken. Samples or specimens are collected so as to minimize the chance of contamination of the sample or specimen by external elements, or the environment by the sample or specimen if it contains hazardous components. Generally, this is carried out by introducing a sample for analysis, e.g., tissue, blood, saliva, etc., directly into a sample collection chamber within a fluidly closed system. Typically, the prevention of cross-contamination of the sample may be accomplished by directly injecting the sample into the sample collection chamber through a optionally sealable opening, e.g., an injection valve, or a septum. Generally, sealable valves are preferred to reduce any potential threat of leakage during or after sample injection. In addition to the foregoing, the sample collection portion of the device/cartridge may also include reagents and/or treatments for neutralization of infectious agents, stabilization of the specimen or sample, pH adjustments, and the like. Stabilization and pH adjustment treatments may include, e.g. introduction of heparin to prevent clotting of blood samples, addition of buffering agents, addition of protease, preservatives and the like. Such reagents may generally be stored within the sample collection chamber of the device/cartridge or may be stored within a separately accessible chamber, wherein the reagents may be added to or mixed with the sample upon introduction of the sample into the device. These reagents may be incorporated within the device in either liquid or lyophilized form, depending upon the nature and stability of the particular reagent used.

Herein the preferred sample is human or animal feces.

Prior to carrying out amplification reactions on a sample, it will often be desirable to perform one or more sample preparation operations upon the sample. Typically, these sample preparation operations will include such manipulations as extraction of intracellular material, e.g., nucleic acids from whole samples and the like. One or more of these various operations may be readily incorporated into the fluidly closed systems contemplated by the present invention.

For those embodiments where whole cells or other tissue samples are being analyzed, it will typically be necessary to extract the nucleic acids from the cells, feces, blood or other bodily fluids prior to continuing with the various sample preparation operations. Accordingly, following sample collection, nucleic acids may be liberated from the collected cells, into a crude extract, followed by additional treatments to prepare the sample for subsequent operations, e.g., denaturation of contaminating (DNA binding) proteins, purification, filtration, desalting, and the like. Liberation of nucleic acids from the sample cells, and denaturation of DNA binding proteins may generally be performed by chemical, physical, or electrolytic lysis methods. For example, chemical methods generally employ lysing agents to disrupt the cells and extract the nucleic acids from the cells, followed by treatment of the extract with chaotropic salts such as guanidinium isothiocyanate or urea to denature any contaminating and potentially interfering proteins. Generally, where chemical extraction and/or denaturation methods are used, the appropriate reagents may be incorporated within a sample preparation chamber, a separate accessible chamber, or may be externally introduced.

Physical methods may be used to extract the nucleic acids and denature DNA binding proteins. U.S. Pat. No. 5,304,481 discusses the use of physical protrusions within microchannels or sharp edged particles within a chamber or channel to pierce cell membranes and extract their contents. Combinations of such structures with piezoelectric elements for agitation can provide suitable shear forces for lysis. Such elements are described in greater detail with respect to nucleic acid fragmentation, below. More traditional methods of cell extraction may also be used, e.g., employing a channel with restricted cross-sectional dimension which causes cell lysis. Alternatively, cell extraction and denaturing of contaminating proteins may be carried out by applying an alternating electrical current to the sample. More specifically, the sample of cells is flowed through a microtubular array while an alternating electric current is applied across the fluid flow. A variety of other methods may be utilized within the device of the present invention to perform cell lysis/extraction, including, e.g., subjecting cells to ultrasonic agitation, or forcing cells through small apertures, thereby subjecting the cells to high shear stress resulting in rupture.

Following extraction, it will often be desirable to separate the nucleic acids from other elements of the crude extract, e.g., denatured proteins, cell membrane particles, salts, and the like. Removal of particulate matter is generally accomplished by filtration, flocculation or the like. A variety of filter types may be readily incorporated into the device. Further, where chemical denaturing methods are used, it may be desirable to desalt the sample prior to proceeding to the next step. Desalting of the sample, and isolation of the nucleic acid may generally be carried out in a single step, e.g., by binding the nucleic acids to a solid phase and washing away the contaminating salts or performing gel filtration chromatography on the sample, passing salts through dialysis membranes, and the like. Suitable solid supports for nucleic acid binding include, e.g., diatomaceous earth, silica (i.e., glass wool), or the like. Suitable gel exclusion media, also well known in the art, may also be readily incorporated into the device/cartridge of the present invention, and is commercially available from, e.g., Pharmacia and Sigma Chemical.

The isolation and/or gel filtration/desalting may be carried out in an additional chamber, or alternatively, the particular chromatographic media may be incorporated in a channel or fluid passage leading to a subsequent reaction chamber. Alternatively, the interior surfaces of one or more fluid passages or chambers may themselves be derivatized to provide functional groups appropriate for the desired purification, e.g., charged groups, affinity binding groups and the like. Alternatively, desalting methods may generally take advantage of the high electrophoretic mobility and negative charge of DNA compared to other elements. Electrophoretic methods may also be utilized in the purification of nucleic acids from other cell contaminants and debris. In one example, a separation channel or chamber of the device is fluidly connected to two separate "field" channels or chambers having electrodes, e.g., platinum electrodes, disposed therein. The two field channels are separated from the separation channel using an appropriate barrier or "capture membrane" which allows for passage of current without allowing passage of nucleic acids or other large molecules. The barrier generally serves two basic functions: first, the barrier acts to retain the nucleic acids which migrate toward the positive electrode within the separation chamber; and second, the barriers prevent the adverse effects associated with electrolysis at the electrode from entering into the reaction chamber (e.g., acting as a salt junction). Such barriers may include dialysis membranes, dense gels, PEI filters, or other suitable materials. Upon application of an appropriate electric field, the nucleic acids present in the sample will migrate toward the positive electrode and become trapped on the capture membrane. Sample impurities remaining free of the membrane are then washed from the chamber by applying an appropriate fluid flow. Upon reversal of the voltage, the nucleic acids are released from the membrane in a substantially purer form. The field channels may be disposed on the same or opposite sides or ends of a separation chamber or channel, and may be used in conjunction with mixing elements described herein, to ensure maximal efficiency of operation. Further, coarse filters may also be overlaid on the barriers to avoid any fouling of the barriers by particulate matter, proteins or nucleic acids, thereby permitting repeated use. In a similar aspect, the high electrophoretic mobility of nucleic acids with their negative charges, may be utilized to separate nucleic acids from contaminants by utilizing a short column of a gel or other appropriate matrix or gel which will slow or retard the flow of other contaminants while allowing the faster nucleic acids to pass.

In a preferred embodiment the probes and/or primers are distributed in the channels or chambers as follows: A specific mix of primers and probes is stably stored as dried material in each individual PCR chamber. With the filling of the PCR chamber with the premixed template/PCR reaction mix the stored primers/probes form a homogeneous solution with concentrations optimal for their designated reactions.

The invention claimed is:

1. A system comprising:
a PCR module configured to receive a sample, the PCR module comprising:
    a plurality of channels, and
    a plurality of PCR chambers,
    each channel leading to a separate PCR chamber to prevent interaction between chambers,
first primers and/or probes, each of the first primers and/or probes being disposed within one of the plurality of PCR chambers, the first primers and/or probes comprising:
    a primer and/or probe having a sequence configured to amplify a cytotoxin tcdB gene;
    a primer and/or probe having a sequence configured to amplify a tcdA gene having a 1.8 kb deletion in the tcdA gene;
    at least one primer and/or probe having a sequence configured to produce at least one tcdC amplicon, wherein the at least one tcdC amplicon has an 18 bp deletion in SEQ ID NO: 1 from nucleotide 330 to nucleotide 347 of a tcdC gene; a 39 bp deletion in SEQ ID NO: 1 from nucleotide 341 to nucleotide 370 of the tcdC gene; and a single nucleotide deletion at position 117 of SEQ ID NO: 1;
second primers and/or probes, each of the second primers and/or probes being disposed within one of the plurality of channels and PCR chambers; and
at least one detector that detects, with the first primers and/or probes:
    the cytotoxin tcdB gene;
    the 1.8 kb deletion in the tcdA gene;
    the 18 bp deletion in SEQ ID NO: 1 from nucleotide 330 to nucleotide 347 of the tcdC gene;
    the 39 bp deletion in SEQ ID NO: 1 from nucleotide 341 to nucleotide 370 of the tcdC gene; and
    the single nucleotide deletion at position 117 of SEQ ID NO: 1; and
wherein the at least one detector detects, with the second primers and/or probes, the binary toxin cdtA/B gene.

2. A system comprising:
a PCR module configured to receive a sample, the PCR module comprising:
    a plurality of channels, and
    a plurality of PCR chambers,
    each channel leading to a separate PCR chamber to prevent interaction between chambers,
    primers and/or probes, each of the primers and/or probes being disposed within one of the plurality of PCR chambers, the primers and/or probes comprising:
        a primer and/or probe configured to amplify a cytotoxin tcdB gene;
        a primer and/or probe configured to amplify a tcdC gene;
        at least one primer and/or probe having a sequence configured to produce at least one tcdC amplicon, wherein the at least one tcdC amplicon has an 18 bp deletion in SEQ ID NO: 1 from nucleotide 330 to nucleotide 347; a 36 bp deletion in SEQ ID NO: 1 from nucleotide 301 to nucleotide 336; a 39 bp deletion in SEQ ID NO: 1 from nucleotide 341 to nucleotide 370; a 54 bp deletion in SEQ ID NO: 1 from nucleotide 313 to nucleotide 366; and a single nucleotide deletion at position 117 of SEQ ID NO: 1; and
at least one detector that detects, with the primers and/or probes:
    the cytotoxin tcdB gene;
    the tcdC gene;
    the 18 bp deletion in SEQ ID NO: 1 from nucleotide 330 to nucleotide 347;
    the 36 bp deletion in SEQ ID NO: 1 from nucleotide 301 to nucleotide 336;
    the 39 bp deletion in SEQ ID NO: 1 from nucleotide 341 to nucleotide 370;
    the 54 bp deletion in SEQ ID NO: 1 from nucleotide 313 to nucleotide 366; and
    the single nucleotide deletion at position 117 of SEQ ID NO: 1.

3. The system of claim 2, wherein each chamber contains at least one of said primers and/or probes configured to perform a designated reaction.

4. The system of claim 2, further comprising:
a lysis module configured to receive a sample,
a fluid transport module configured to transport reagents to the lysis module, and
a fluid pathway carrying the sample from the lysis module to the plurality of channels in the PCR module.

5. A system comprising:
primers, the primers comprising:
    a primer having a sequence configured to amplify a cytotoxin tcdB gene;
    a primer having a sequence complementary to a tcdA gene sequence having a 1.8 kb deletion in the tcdA gene;
    at least one primer having a sequence complementary to a tcdC gene sequence, wherein the tcdC gene sequence has at least one of:
        an 18 bp deletion in SEQ ID NO: 1 from nucleotide 330 to nucleotide 347 of a tcdC gene;

a 39 bp deletion in SEQ ID NO: 1 from nucleotide 341 to nucleotide 370 of the tcdC gene; and
a single nucleotide deletion at position 117 of SEQ ID NO: 1;
a PCR module configured to receive a sample, the PCR module comprising a plurality of PCR chambers, each PCR chamber containing at least one of said primers, wherein at least two PCR chambers contain a different one of said primers:
at least one detector that detects, with the primers:
the cytotoxin tcdB gene;
the 1.8 kb deletion in the tcdA gene;
the 18 bp deletion in SEQ ID NO: 1 from nucleotide 330 to nucleotide 347 of the tcdC gene;
the 39 bp deletion in SEQ ID NO: 1 from nucleotide 341 to nucleotide 370 of the tcdC gene; and
the single nucleotide deletion at position 117 of SEQ ID NO: 1.

\* \* \* \* \*